(12) United States Patent
Darras et al.

(10) Patent No.: US 11,464,916 B2
(45) Date of Patent: *Oct. 11, 2022

(54) CAP FOR A MEDICAMENT CONTAINER

(71) Applicant: Sanofi, Paris (FR)

(72) Inventors: David Darras, Paris (FR); Fabien Canepa, Paris (FR); Bruno Serre, Paris (FR); Jacky Mazzolini, Villard Saint Sauveur (FR)

(73) Assignee: Sanofi, Paris (FR)

( * ) Notice: Subject to any disclaimer, the term of this patent is extended or adjusted under 35 U.S.C. 154(b) by 378 days.

This patent is subject to a terminal disclaimer.

(21) Appl. No.: 16/675,949

(22) Filed: Nov. 6, 2019

(65) Prior Publication Data

US 2020/0061305 A1 Feb. 27, 2020

Related U.S. Application Data

(63) Continuation of application No. 14/914,391, filed as application No. PCT/EP2014/068131 on Aug. 27, 2014, now Pat. No. 10,500,347.

(30) Foreign Application Priority Data

Aug. 29, 2013 (EP) .................................... 13306180

(51) Int. Cl.
*A61M 5/32* (2006.01)
*A61M 5/31* (2006.01)

(52) U.S. Cl.
CPC ........ *A61M 5/3202* (2013.01); *A61M 5/3204* (2013.01); *A61M 5/326* (2013.01);
(Continued)

(58) Field of Classification Search
CPC .............. A61M 5/3202; A61M 5/3204; A61M 5/3205; A61M 5/321; A61M 5/3213;
(Continued)

(56) References Cited

U.S. PATENT DOCUMENTS 6,921,383 B2 7/2005 Vitello
6,984,223 B2 1/2006 Newby et al.
(Continued)

FOREIGN PATENT DOCUMENTS

CA 2840912 1/2013
CN 101259298 9/2008
(Continued)

OTHER PUBLICATIONS

Definition of surface (Merriam Webster) Jul. 13, 2018.
(Continued)

*Primary Examiner* — Dung T Ulsh
(74) *Attorney, Agent, or Firm* — Fish & Richardson P.C.

(57) ABSTRACT

Described is a cap for covering a needle shield on a needle of a medicament container, the cap comprising a cylindrical portion having a first outer diameter, a disc portion disposed on a distal end of the cylindrical portion, the disc portion having a second outer diameter larger than the first outer diameter, and a gripping surface disposed on an inner surface of the cylindrical portion and adapted to a frictionally engage a needle shield on a needle.

20 Claims, 6 Drawing Sheets

Specification includes a Sequence Listing.

(52) U.S. Cl.
CPC .......... *A61M 2005/3139* (2013.01); *A61M 2005/3264* (2013.01); *A61M 2205/583* (2013.01)

(58) Field of Classification Search
CPC .......... A61M 5/3243; A61M 5/3245; A61M 5/3271; A61M 2005/3215; A61B 5/150259; A61B 5/150351; A61B 5/150534; A61B 5/150633; A61B 5/150694; A61B 5/150717
See application file for complete search history.

(56) References Cited

U.S. PATENT DOCUMENTS

| | | |
|---|---|---|
| 6,986,760 B2 | 1/2006 | Giambattista et al. |
| 7,674,246 B2 | 3/2010 | Gillespie et al. |
| 7,815,061 B1* | 10/2010 | Robinson ............ B65D 50/043 215/221 |
| 7,931,626 B2 | 4/2011 | Kirchhofer et al. |
| 8,251,947 B2 | 8/2012 | KrMar et al. |
| 8,287,489 B2 | 10/2012 | Schuster et al. |
| 8,313,470 B2 | 11/2012 | Abry |
| 8,361,025 B2 | 1/2013 | Lawlis et al. |
| 8,641,668 B2 | 2/2014 | Matusch |
| 8,708,968 B2 | 4/2014 | Julian et al. |
| 8,814,828 B2 | 8/2014 | Llewllyn-Hyde et al. |
| 8,945,067 B2 | 2/2015 | McLoughlin et al. |
| 8,992,472 B2 | 3/2015 | Pongpairochana |
| 8,992,477 B2 | 3/2015 | Raday et al. |
| 9,028,451 B2 | 5/2015 | Jennings |
| 9,061,104 B2 | 6/2015 | Daniel |
| 9,238,111 B2 | 1/2016 | Marshall et al. |
| 9,242,050 B2 | 1/2016 | Abry |
| 9,327,083 B2 | 5/2016 | Giambattista et al. |
| 9,339,610 B2 | 5/2016 | Julian et al. |
| 9,522,233 B2 | 12/2016 | Bicknell et al. |
| 2002/0193746 A1 | 12/2002 | Chevallier |
| 2003/0181859 A1 | 9/2003 | Brunel |
| 2006/0100588 A1 | 5/2006 | Brunnberg et al. |
| 2008/0269690 A1 | 10/2008 | Felix-Faure |
| 2009/0054849 A1 | 2/2009 | Burnell et al. |
| 2010/0016795 A1 | 1/2010 | McLoughlin |
| 2010/0160894 A1 | 6/2010 | Julian et al. |
| 2010/0185178 A1 | 7/2010 | Sharp et al. |
| 2010/0195936 A1 | 8/2010 | Ackerman |
| 2010/0268169 A1 | 10/2010 | Llewellyn-Hyde et al. |
| 2010/0286619 A1* | 11/2010 | Abry ............... A61M 5/2033 604/192 |
| 2012/0107783 A1 | 5/2012 | Julian et al. |
| 2013/0053788 A1 | 2/2013 | Dugand et al. |
| 2013/0096462 A1 | 4/2013 | West |
| 2014/0257192 A1 | 9/2014 | Morgan et al. |
| 2014/0330207 A1 | 11/2014 | McLoughlin et al. |
| 2014/0336588 A1 | 11/2014 | McLoughlin et al. |
| 2014/0343504 A1 | 11/2014 | Bicknell et al. |
| 2015/0045729 A1 | 2/2015 | Denzer |
| 2015/0174325 A1* | 6/2015 | Young ............ A61M 5/2033 604/135 |
| 2016/0106929 A1* | 4/2016 | Fournier ........... A61M 5/3202 604/192 |
| 2016/0144132 A1* | 5/2016 | Scanlon ........... A61M 5/3202 604/192 |
| 2016/0193416 A1* | 7/2016 | Olson ............. A61M 5/3158 604/192 |
| 2016/0325044 A1 | 11/2016 | Tschirren et al. |

FOREIGN PATENT DOCUMENTS

| | | |
|---|---|---|
| CN | 101868275 | 10/2010 |
| CN | 102361660 | 2/2012 |
| EP | 2520318 | 7/2012 |
| EP | 3038682 | 8/2014 |
| GB | 2469671 | 10/2010 |
| JP | 2008-307369 | 12/2008 |
| JP | 2008-543500 | 12/2008 |
| JP | 2009-542334 | 12/2009 |
| JP | 2010-540054 | 12/2010 |
| WO | WO 2005/070481 | 8/2005 |
| WO | WO 2007/002052 | 1/2007 |
| WO | WO 2009/040601 | 4/2009 |
| WO | WO 2012/073032 | 6/2012 |
| WO | WO 2012/145685 | 10/2012 |
| WO | WO 2013/009387 | 1/2013 |
| WO | WO 2013/011006 | 1/2013 |
| WO | WO 2015/028488 | 3/2015 |

OTHER PUBLICATIONS

International Preliminary Report and Written Opinion in International Application No. PCT/EP2014/068131, dated Aug. 27, 2014, 11 pages.

International Preliminary Report on Patentability in International Application No. PCT/EP2014/068131, dated Aug. 27, 2014, 8 pages.

Rote Liste, "50. Hypophysen-, Hypothalamushormone, andere regulatorische Peptide u. ihre Hemmstoffe," Chapter 50, ed. 2008, 20 pages.

* cited by examiner

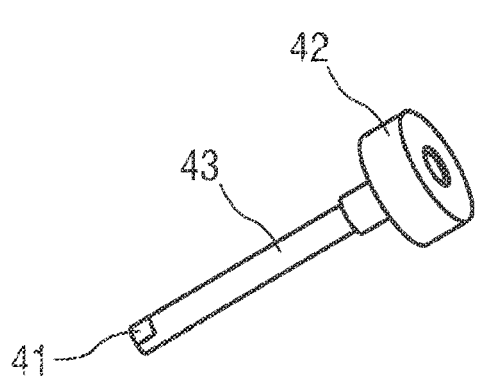
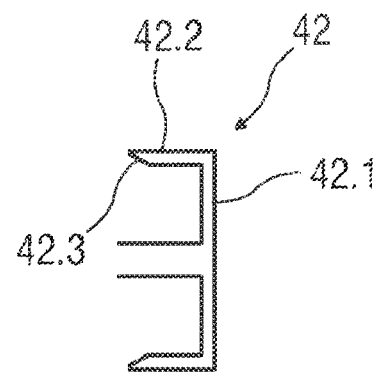
FIG 4A  FIG 4B
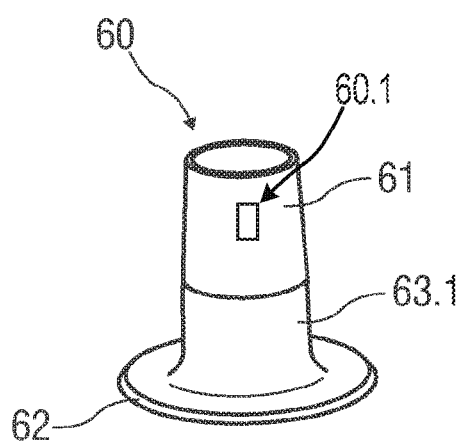
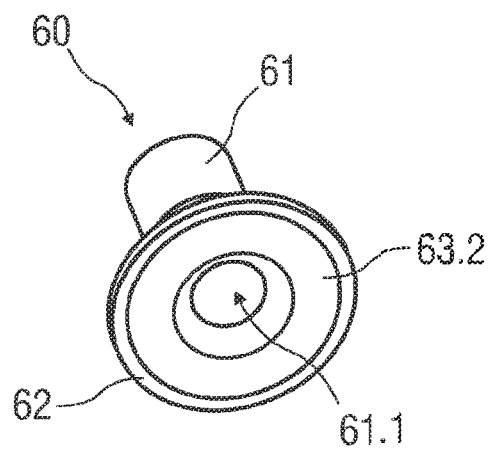
FIG 5A  FIG 5B

CAP FOR A MEDICAMENT CONTAINER

CROSS-REFERENCE TO RELATED APPLICATIONS

This application is a continuation of Ser. No. 14/914,391, filed on Feb. 25, 2016, which is a U.S. national stage application under 35 USC § 371 of International Application No. PCT/EP2014/068131, filed on Aug. 27, 2014, which claims priority to European Patent Application No. 13306180.4, filed on Aug. 29, 2013, the entire contents of which are incorporated herein by reference.

TECHNICAL FIELD

The invention relates to a cap for a medicament container.

BACKGROUND OF THE INVENTION

Administering an injection is a process which presents a number of risks and challenges for users and healthcare professionals, both mental and physical. Medicament delivery devices typically fall into two categories—manual devices and autoinjectors. In a conventional manual device, manual force is required to drive a medicament through a needle. This is typically done by some form of button/plunger that has to be continuously pressed during the injection. A conventional auto-injector may provide the force for administering the medicament by a spring, and a trigger button or other mechanism may be used to activate the injection.

For use of manual devices and autoinjectors, safety and usability are of the utmost importance. Thus, there remains a need for improved medicament delivery devices which include components or mechanisms for user and patient safety (e.g., to prevent misuse, needlestick, etc.) and enhanced usability (e.g., making the device easier to user before, during and after an injection to improve dose accuracy and compliance).

WO 2012/145685 A1 discloses an auto-injector apparatus which comprises a single-use cassette and an auto-injector. The cassette comprises a housing and a sleeve movably disposed in the housing. A syringe may be disposed in the sleeve and secured therein with a lock cap. The lock cap is affixed to a distal end of the sleeve and contacts the distal end of the syringe. A shield remover extends through an opening in a proximal end of the housing for removing a needle shield which covers a needle of the syringe. A cassette identification arrangement is provided on a surface of the housing to enable the auto-injector to identify the cassette. The auto-injector is provided with a detector for reading the cassette identification arrangement.

US 2010/185178 A1 discloses an injection device including a syringe having a needle, a barrel and a plunger. The device is configured to provide an automatic injection cycle and includes a drive coupling arrangement between a driving spring and the syringe. In operation, a drive force can be selectively transmitted between the respective first and second parts of the drive coupling arrangement depending upon their relative rotational positions such that, when the first and second parts are in a first relative rotational position during the dispensing stage, a driving force is transmitted to the plunger to drive the plunger into the barrel, and, when the first and second parts are in a second relative rotational position during the retraction stage, no force is transmitted to the plunger to allow the plunger and the syringe to retract.

SUMMARY OF THE INVENTION

Aspects of the present invention may include an improved cap for a medicament container.

In an exemplary embodiment, a cap for covering a needle shield on a needle of a medicament container according to the present invention comprises a cylindrical portion having a first outer diameter, a disc portion disposed on a distal end of the cylindrical portion and having a second outer diameter larger than the first outer diameter, and a gripping surface disposed on an inner surface of the cylindrical portion and adapted to frictionally engage a needle shield on a needle.

In an exemplary embodiment the engagement of the gripping surface to the needle shield can be purely or exclusively frictional.

In an exemplary embodiment, the gripping surface further comprises a proximal portion disposed on an outer surface of the cylindrical portion and a proximal surface of the disc portion.

In an exemplary embodiment, the gripping surface further comprises a distal portion disposed on a distal surface of the disc portion.

In an exemplary embodiment, the gripping surface is made from a first material and the cylindrical portion and the disc portion are made from a second material, and the first material has a lower durometer than the second material.

In an exemplary embodiment, the proximal portion or the distal portion includes one or more frictional features.

In an exemplary embodiment, the gripping surface disposed on the inner surface of the cylindrical portion has a thickness that decreases from a distal end to a proximal end.

In an exemplary embodiment, the gripping surface includes a ramp feature on the proximal end.

In an exemplary embodiment, the cap further comprises an indicia disposed on the cylindrical portion, the disc portion and/or the gripping surface. The indicia may include one or more of a word or a symbol.

In an exemplary embodiment, a medicament container according to the present invention comprises a barrel, a needle disposed on a distal end of the barrel, a needle shield coupled to the needle, and a cap coupled to the needle shield, wherein the cap is according to any of the disclosed embodiments. The needle shield comprises a sheath made from a third material. The needle shield comprises a casing made from a fourth material different from the third material and disposed on the sheath. The third material may be rubber or elastomer latex and the fourth material may be polypropylene or acrylonitrile butadiene styrene.

In an exemplary embodiment, a medicament delivery device according to the present invention comprises a medicament container according to any of the disclosed embodiments, a safety device adapted to cover the needle of the medicament container, and a finger flange coupled to the safety device.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIGS. 4A and 4B show an exemplary embodiment of a plunger according to the present invention, FIGS. 5A and 5B show an exemplary embodiment of a cap according to the present invention.

DETAILED DESCRIPTION

Figure 1:
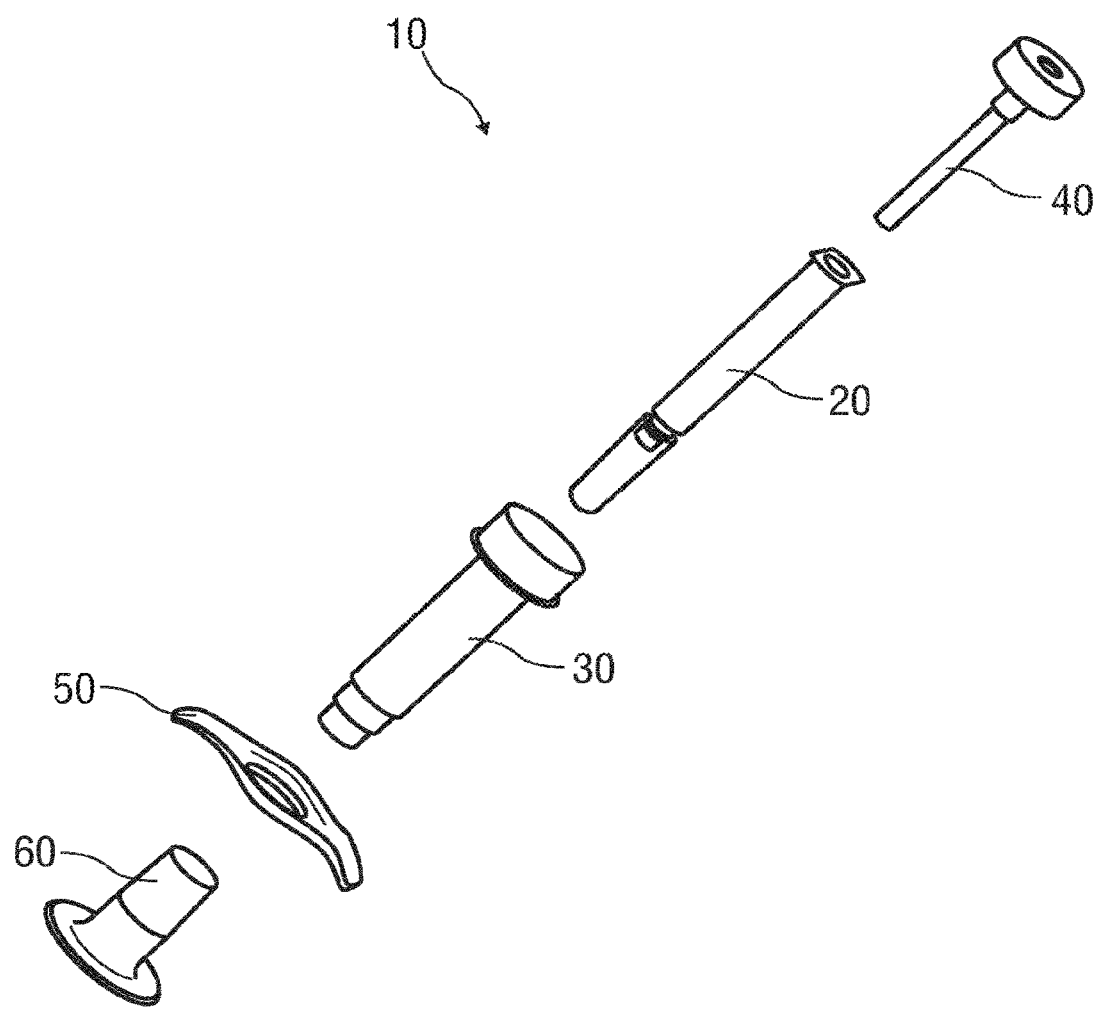
FIG. 1 shows an exemplary embodiment of a medicament delivery device according to the present invention.

FIG. 1 shows an exemplary embodiment of a medicament delivery device 10 according to the present invention. In an exemplary embodiment, the delivery device 10 comprises a medicament container 20, a safety device 30 and a plunger 40. The delivery device 10 may further include a finger flange 50 and/or a cap 60.

Figure 2:
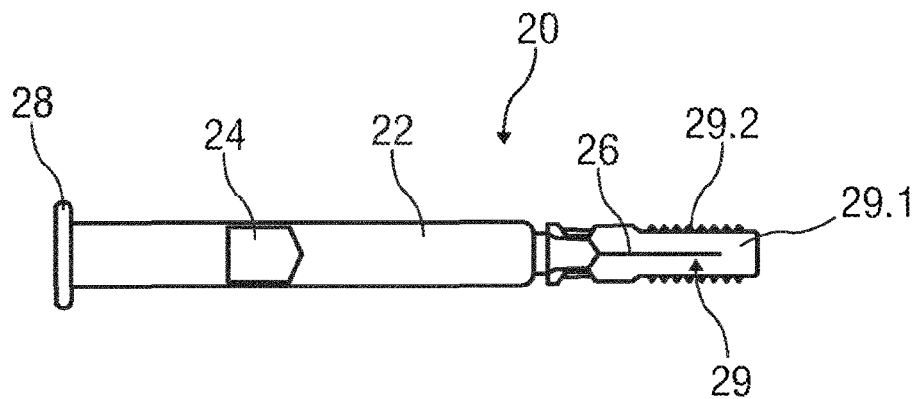
FIG. 2 shows an exemplary embodiment of a medicament container according to the present invention.

FIG. 2 shows an exemplary of a medicament container 20 according to the present invention. In the exemplary embodiment, the medicament container 20 includes a barrel 22, a stopper 24 slidably disposed in the barrel 22 and a needle 26 coupled to a distal end of the barrel 22. In an exemplary embodiment, the stopper 24 may be made from a rubber material. A proximal end of the barrel 22 includes a flange 28 which may be fully or partial circular, elliptical, square, rectangular or any other shape. The barrel 22 may be any size (e.g., 0.5 ml, 1 ml, 2 ml, etc.) and be made of any suitable material (e.g., plastic, glass). In an exemplary embodiment, the barrel 22 may be manufactured from Type I clear glass. In an exemplary embodiment, the stopper 24 is made from a rubber material. In an exemplary embodiment, the needle 26 is made from stainless steel. The needle 26 may be any gauge or length.

In an exemplary embodiment, a needle shield 29 may be removably coupled to the distal end of the barrel 22 to cover the needle 26. In an exemplary embodiment, the needle shield 29 may be a sheath 29.1 made of, for example, rubber or elastomer latex. In another exemplary embodiment, the needle shield 29 may further include a casing 29.2 made of, for example, polypropylene or acrylonitrile butadiene styrene or any other similar material. The casing 29.2 may be disposed partially or entirely on an outer surface of the sheath 29.1. The casing 29.2 may provide further support to the sheath 29.1 to, for example, prevent the needle 26 from bending or puncturing the sheath 29.1. When the needle shield 29 is removed, the needle 26 is exposed.

Figure 3:
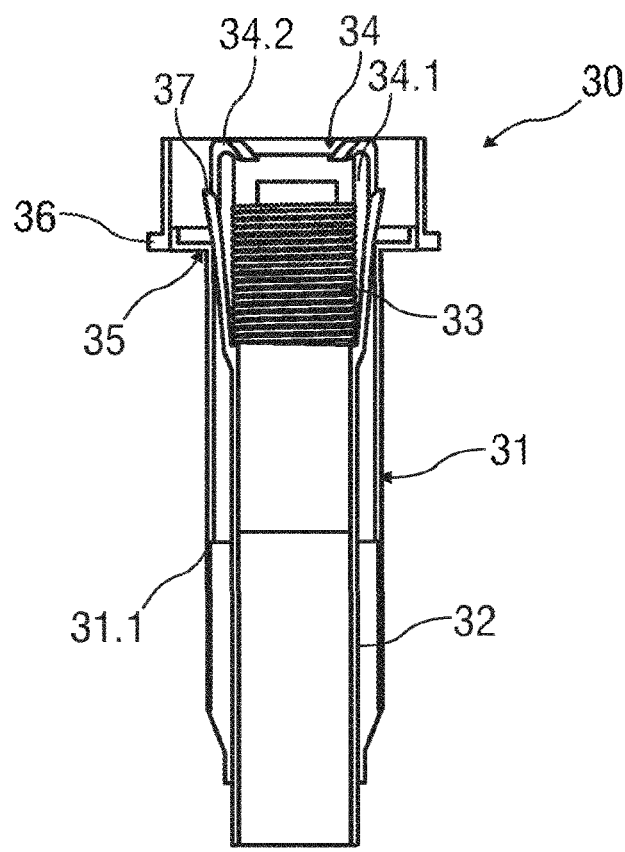
FIG. 3 shows an exemplary embodiment of a safety device according to the present invention.

FIG. 3 shows an exemplary embodiment of a safety device 30 according to the present invention. In the exemplary embodiment, the safety device 30 comprises a first sheath 31 arranged telescopically with a second sheath 32, and the sheaths 31, 32 which are biased relative to each other by a spring 33. Prior to use, one of the sheaths is in a retracted position relative to the other sheath, and after use, the one of the sheaths is in an extended position relative to the other sheath to cover the needle 26. In the extended position, the one of the sheaths is locked in the extended position to prevent retraction and uncovering of the needle 26.

In the exemplary embodiment shown in FIG. 3, the first sheath 31 is an outer sheath, and the second sheath 32 is an inner sheath, and the second sheath 32 is movable from the retracted position to the extended position relative to the first sheath 31. The first sheath 31 comprises an open distal end allowing the second sheath 32 to move from the retracted position to the distal position. A proximal end of the first sheath 31 includes an engagement arrangement 34 adapted to engage the flange 28 of the medicament container 20. In an exemplary embodiment, the engagement arrangement 34 includes a support surface 34.1 adapted to abut a distal surface of the flange 28 to prevent distal movement of the medicament container 20 relative to the first sheath 31, and one or more resilient hooks 34.2 adapted to engage the flange 28 to prevent proximal movement of the medicament container 20 relative to the first sheath 31. When the medicament container 20 is inserted into the first sheath 31, the flange 28 causes the resilient hooks 34.2 to deflect until the flange 28 is distal of the hooks 34.2, at which point the hooks 34.2 return to a non-deflected position and can abut a proximal surface of the flange 28.

In an exemplary embodiment, the proximal end of the first sheath 31 includes an inner ledge 35 and an outer ledge 36. The inner ledge 35 may be formed partially or entirely around a proximal opening of the first sheath 31. The outer ledge 36 may be formed partially or entirely around an outer surface of the first sheath 31. As shown in the exemplary embodiment in FIG. 3, the first sheath 31 may have a distal portion having a first outer diameter and a proximal portion having a second outer diameter which is larger than the first outer diameter. The outer ledge 36 may be formed partially or entirely around the larger second outer diameter to provide a support surface for a user's fingers.

In an exemplary embodiment, the second sheath 32 comprises an open distal end allowing the needle 26 to pass through when the second sheath 32 is in the retracted position. A proximal end of the second sheath 32 includes one or more resilient arms 37 adapted to releaseably engage the inner ledge 35 to maintain the second sheath 32 in the retracted position against the force of the spring 33 which biases the second sheath 32 towards the extended position. When the second sheath 32 is in the retracted position, the resilient arms 37 are radially biased to engage the inner ledge 35.

In an exemplary embodiment, the first sheath 31 is made from polycarbonate, the second sheath is made from copolyester, and the spring 33 is made from stainless steel.

FIGS. 4A and 4B show an exemplary embodiment of a plunger 40 according to the present invention. In the exemplary embodiment, the plunger 40 includes a distal end 41 adapted to engage the stopper 24, a proximal end 42 adapted to be pressed by a user, and a stem 43 connecting the distal and proximal ends 41, 42. FIG. 4B shows a partial cross-section of an exemplary embodiment of the proximal end 42 of the plunger 40. In the exemplary embodiment, the proximal end 42 includes a bearing surface 42.1 adapted to receive a user's finger. The bearing surface 42.1 may be flat (perpendicular relative to a longitudinal axis of the medicament container 20) or have a partially or entirely concave or convex surface. In another exemplary embodiment, the bearing surface 42.1 may have one or more surface elements (e.g., ridges, bumps, etc.) adapted to frictionally engage the user's finger to prevent it from slipping off the bearing surface 42.1 during use. The proximal end 42 further includes a radial surface 42.2 having a distal end that is adapted to engage one or more resilient projections on the first sheath 31 that deflect upon engagement with the radial surface 42.2 to engage the one or more resilient arms 37 on the second sheath 32 when the plunger 40 has been pressed a sufficient distance relative to the medicament container 20. In an exemplary embodiment, the distal end of the radial surface 42.2 may comprise one or more ramps 42.3 adapted to engage the resilient projections such that the resilient rejections resilient arms 37 deflect and disengage the inner ledge 35.

In an exemplary use, when the plunger 40 is pressed a sufficient distance, the ramps 42.3 engage the resilient projections which engage the resilient arms 37 such that the resilient arms 37 deflect and disengage the inner ledge 35. The force of the spring 33 pushes the second sheath 32 distally relative to the first sheath 31 from the retracted position to the extended position. The second sheath 32 is locked in the extended position, because the resilient arms 37 abut a stop surface 31.1 (shown in FIG. 3) on the first sheath 31 preventing the second sheath 32 from moving proximally relative to the first sheath 31 from the extended position.

In an exemplary embodiment, the plunger 40 is made from polypropylene or acrylonitrile butadiene styrene.

In an exemplary embodiment, the safety device 30 and the plunger 40 may be as described in U.S. Patent Application Publication No. 2002/0193746, the entire disclosure of which is expressly incorporated herein by reference.

FIGS. 5A and 5B show an exemplary embodiment of a cap 60 according to the present invention. In the exemplary embodiment, the cap 60 comprises cylindrical portion 61 having a first outer diameter and a disc portion 62 having a second outer diameter larger than the second outer diameter. The cylindrical portion 61 includes a thru hole 61.1 adapted to accommodate the needle shield 29. The disc portion 62 may include a thru hole coaxial with the thru hole 61.1 or may include a full or partial cover to fully or partially enclose the thru hole 61.1. When assembled a proximal end of the cylindrical portion 61 may abut a distal end of the first sheath 31.

In an exemplary embodiment, the cap 60 may be made from polypropylene or acrylonitrile butadiene styrene.

In an exemplary embodiment, a gripping surface 63 may be coupled to the cap 60. In the exemplary embodiment, the gripping surface 63 includes a proximal portion 63.1 and a distal portion 63.2. The proximal portion 63.1 may be coupled to all or part of an outer surface of the cylindrical portion 61 of the cap 60 and/or all or part of a proximal surface of the disc portion 62. The distal portion 63.2 may be coupled to all of part of an inner surface of the cylindrical portion 61 of the cap 60 and/or all or part of a distal surface of the disc portion 62. In another exemplary embodiment, the proximal portion 63.1 or the distal portion 63.2 may be disposed partially or entirely around a circumference of the disc portion 62.

In an exemplary embodiment, the gripping surface 63 may be made from a material having a lower durometer than the material comprising the cap 60. In an exemplary embodiment, the gripping surface 63 may be elastomer thermoplastic. The gripping surface 63 may provide an easily grippable and supportive surface for a user to grip to remove the cap 60 from the medicament delivery device 10. In an exemplary embodiment, any part of the gripping surface 63 may include one or more frictional features (e.g., ridges, bumps, etc.) to ensure that the user's fingers do not slip when gripping and removing the cap 60.

Figure 6:
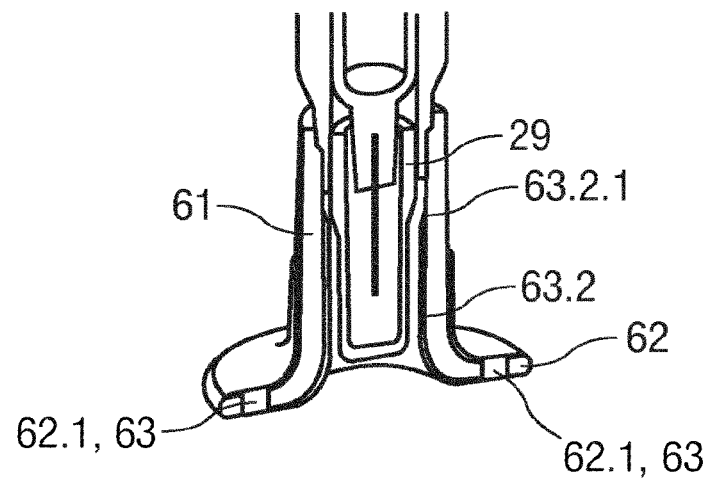
FIG. 6 shows an exemplary embodiment of a cap according to the present invention.

FIG. 6 shows an exemplary embodiment of a cap 60 coupled to the medicament delivery device 10. In the exemplary embodiment, the distal portion 63.2 of the gripping surface 63 is partially disposed on the inner surface of the cylindrical portion 61 of the cap 60. In an exemplary embodiment, a thickness of the distal portion 63.2 may decrease along the length of the inner surface in the proximal direction. A proximal end of the distal portion 63.2 along the length of the inner surface may include a ramp feature 63.2.1 adapted to receive and guide the needle shield 29, e.g., during assembly. The distal portion 63.2 of the gripping surface 63 is adapted to frictionally engage the needle shield 29, such that when the cap 60 is pulled away from the medicament delivery device 10, the needle shield 29 is removed. In another exemplary embodiment, all or part of the distal portion 63.2 may include one or more engagement features (e.g., a barb, a hook, a projection, etc.) adapted to engage the needle shield 29 (or any feature thereof, e.g., a slot, a channel, a recess, etc.) when the needle shield 29 is inserted into the cap 60. In an exemplary embodiment, the distal portion 63.2 may include one or more separate pieces of material. For example, a first piece of material may be disposed on the inner surface of the cylindrical portion 61 and a second piece of material may be disposed on the distal surface of the disc portion 62. A thru-hole 62.1 may be formed in the disc portion 62, e.g., for molding the gripping surface 63.

In an exemplary embodiment, the cap 60 and/or the gripping surface 63 may include one or more indicia for indicating how to remove the cap 60. For example, all or part of the cap 60 may be a first color and all or part of the gripping surface 63 may be a second color different from the first color to signify that this is the needle end of the device 10. In another exemplary embodiment, one or more words or symbols may be disposed on the cap 60 and/or the gripping surface 63. For example, an arrow point in the distal direction and/or the words "PULL" or "DO NOT TWIST" may be disposed on the cap 60 and/or the gripping surface 63.

Figure 7:
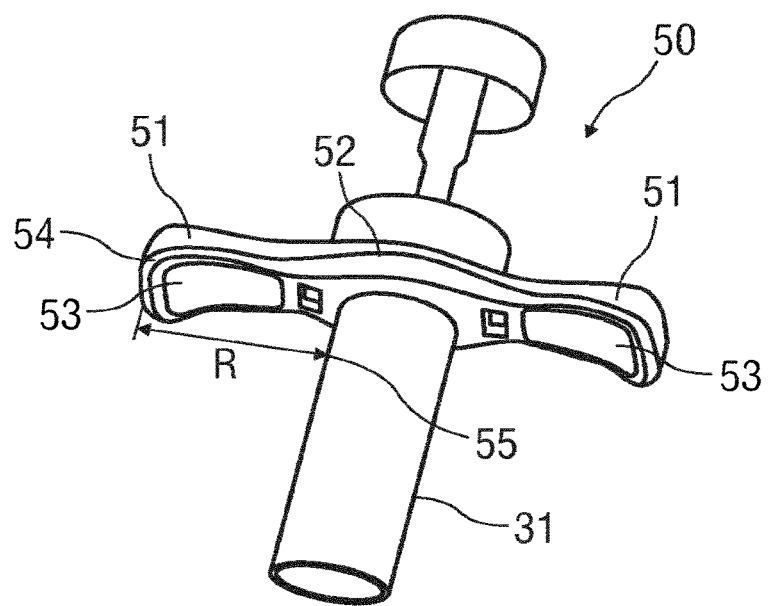
FIG. 7 shows an exemplary embodiment of a finger flange according to the present invention.
Figure 8:
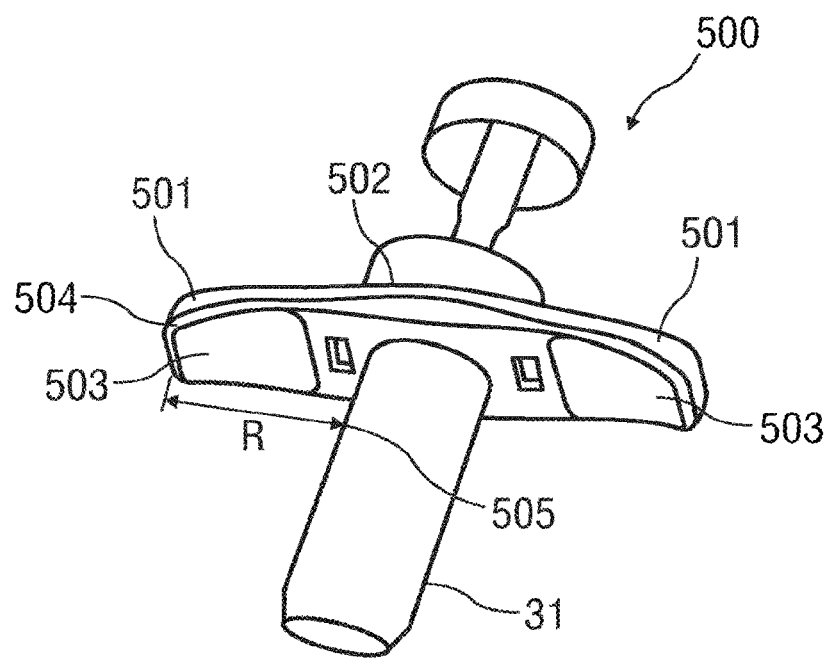
FIG. 8 shows another exemplary embodiment of a finger flange according to the present invention.
Figure 9:
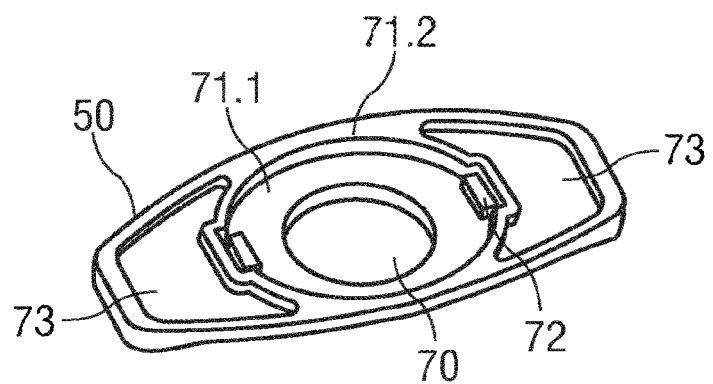
FIG. 9 shows an exemplary embodiment of a finger flange according to the present invention.

FIG. 7 shows an exemplary embodiment a finger flange 50 according to the present invention. FIG. 8 shows another exemplary embodiment of a finger flange 500 according to the present invention. FIG. 9 shows a proximal view of a finger flange 50/500 according to the present invention.

As shown in the exemplary embodiment in FIG. 9, a proximal surface of the finger flange 50/500 include a hole 70 adapted to receive the first sheath 31. In an exemplary embodiment, a diameter of the hole 70 is approximately equal to an outer diameter of the first sheath 31. A central recess 71 may be formed around the hole 70 and be adapted to accommodate a proximal portion of the first sheath 31. For example, the central recess 71 may include a bearing surface 71.1 adapted to abut a distal face of the outer ledge 36. The central recess 71 may further include a retaining wall 71.2 adapted to abut at least a portion of the outer ledge 36 to prevent rotation of the first sheath 31 relative to the finger flange 50/500. One or more resilient clips 72 are disposed within or adjacent the central recess 71 and adapted to engage the outer ledge 36. When the finger flange 50/500 is coupled to the first sheath 31, the clips 72 deflect to accommodate the outer ledge 36 and then return to a non-deflected position to engage the outer ledge 36.

In another exemplary embodiment, the bearing surface 71.1 may not be recessed but may be in plane with the proximal surface of the finger flange 50/500. In this exemplary embodiment, the retaining wall 71.2 and the clips 72 may extend proximally from the flat surface.

In an exemplary embodiment, the proximal surface of the finger flange 50/500 may include one or more lateral recesses 73 adjacent the central recess 71. The lateral recesses 73 may be formed to create a hinge effect when supporting the user's fingers. The lateral recesses 73 may further decrease weight of the finger flange 50/500 and reduce constraints on molding.

FIG. 7 shows an exemplary embodiment of the finger flange 50 disposed on the outer sheath 31. In the exemplary embodiment, the finger flange 50 includes one or more support portions 51 extending radially from a central portion 52. The proximal surface of the finger flange 50 is substantially flat and distal surfaces of the support portions 51 and the central portion 52 are concave relative to the proximal surface (e.g., when the finger flange 50 is placed on a flat surface such that the proximal surface engages the flat surface). The support portion 51 may include a support surface 53. In an exemplary embodiment, the support surface 53 may be made from a material having a lower durometer than the material comprising the finger flange 50. In an exemplary embodiment, the support surface 53 may be elastomer thermoplastic. The gripping surface 53 may provide a surface for a user's finger when administering an injection. In an exemplary embodiment, any part of the support surface 53 may include one or more frictional features (e.g., ridges, bumps, etc.) to ensure that the user's fingers do not slip when administering the injection. While the exemplary embodiment of the invention shows two support portions 51 extending radially in a wing-like fashion from the central portion 52, those of skill in the art will understand that any number of support portions 51 in any shape, size or dimension may be utilized based on the intended application. For example, a radial distance R between an outer radial surface 54 and an inner radial surface 55 may be approximately 20 mm. However, for use with elderly or arthritic patients, the radial distance may be increased, and the support portions may be larger.

In an exemplary embodiment, the finger flange 50 may be made from polypropylene or acrylonitrile butadiene styrene and the support surfaces 53 may be made from elastomer thermoplastic.

FIG. 8 shows an exemplary embodiment of the finger flange 500 disposed on the outer sheath 31. In the exemplary embodiment, the finger flange 500 includes one or more support portions 501 extending radially from a central portion 502. Proximal and distal surfaces of the support portions 501 are concave, and proximal and distal surfaces of the central portion 502 are substantially flat (e.g., approximately perpendicular to a longitudinal axis of the first sheath 31). The support portion 501 may include a support surface 503. In an exemplary embodiment, the support surface 503 may be made from a material having a lower durometer than the material comprising the finger flange 500. In an exemplary embodiment, the support surface 503 may be elastomer thermoplastic. The gripping surface 503 may provide a surface for a user's finger when administering an injection. In an exemplary embodiment, any part of the support surface 503 may include one or more frictional features (e.g., ridges, bumps, etc.) to ensure that the user's fingers do not slip when administering the injection. While the exemplary embodiment of the invention shows two support portions 501 extending radially in a wing-like fashion from the central portion 502, those of skill in the art will understand that any number of support portions 501 in any shape, size or dimension may be utilized based on the intended application. For example, a radial distance R between an outer radial surface 504 and an inner radial surface 505 may be approximately 20 mm. However, for use with elderly or arthritic patients, the radial distance may be increased, and the support portions may be larger.

In an exemplary embodiment, the finger flange 500 may be made from polypropylene or acrylonitrile butadiene styrene and the support surfaces 503 may be made from elastomer thermoplastic.

Figure 10:
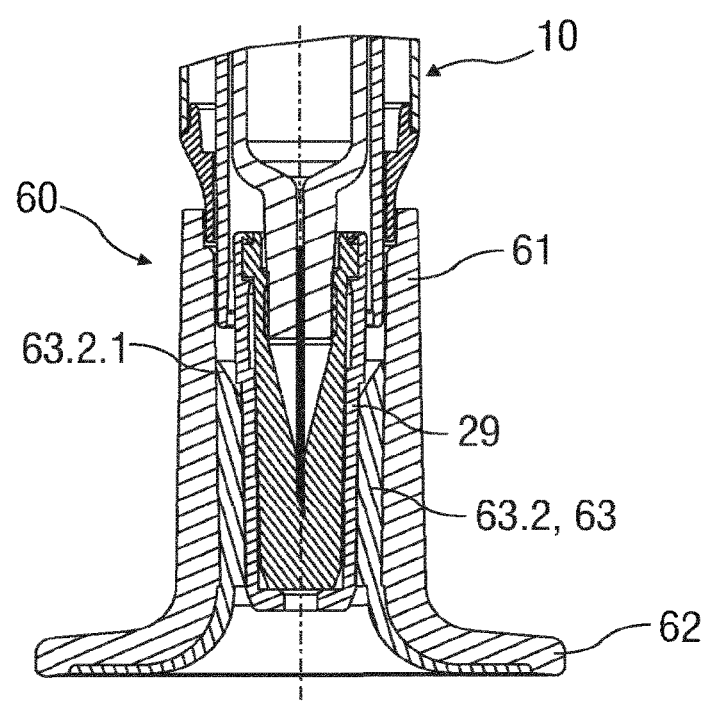
FIG. 10 shows an exemplary embodiment of a cap according to the present invention, Corresponding parts are marked with the same reference symbols in all figures.

FIG. 10 shows an exemplary embodiment of a cap 60 coupled to the medicament delivery device 10. In the exemplary embodiment, the distal portion 63.2 of the gripping surface 63 is at least partially disposed on the inner surface of the cylindrical portion 61 of the cap 60. In an exemplary embodiment, a thickness of the distal portion 63.2 may decrease along the length of the inner surface in the proximal direction. A proximal end of the distal portion 63.2 along the length of the inner surface may include a ramp feature 63.2.1 adapted to receive and guide the needle shield 29, e.g., during assembly. The distal portion 63.2 of the gripping surface 63 is adapted to frictionally engage the needle shield 29, such that when the cap 60 is pulled away from the medicament delivery device 10, the needle shield 29 is removed. In another exemplary embodiment, all or part of the distal portion 63.2 may include one or more engagement features (e.g., a barb, a hook, a projection, etc.) adapted to engage the needle shield 29 (or any feature thereof, e.g., a slot, a channel, a recess, etc.) when the needle shield 29 is inserted into the cap 60. In an exemplary embodiment, the distal portion 63.2 may include one or more separate pieces of material.

In an exemplary embodiment, the cap 60 and/or the gripping surface 63 may include one or more indicia 60.1 for indicating how to remove the cap 60. For example, all or part of the cap 60 may be a first color and all or part of the gripping surface 63 may be a second color different from the first color to signify that this is the needle end of the device 10. In another exemplary embodiment, one or more words or symbols may be disposed on the cap 60 and/or the gripping surface 63. For example, an arrow point in the distal direction and/or the words "PULL" or "DO NOT TWIST" may be disposed on the cap 60 and/or the gripping surface 63.

While exemplary embodiments of the components and/or portions of the cap 60 are described as having certain shapes (e.g., cylinders, discs, etc.) with certain properties that connote a shape (e.g., a diameter, circumference, etc.), those of skill in the art will understand that the cap 60 according to present invention is not limited to any shape or size, but may be adapted for any application or use.

While exemplary embodiments of the present invention are described as being made from certain materials, those of skill in the art will understand that other materials (and/or combinations of materials) may be utilized based on the intended application or use.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

REFERENCES 10 medicament delivery device
20 medicament container
22 barrel
24 stopper
26 needle
28 flange
29 needle shield
29.1 sheath
29.2 casing
30 safety device
31 first sheath
31.1 stop surface
32 second sheath
33 spring
34 engagement arrangement
34.1 support surface
34.2 resilient hook
35 inner ledge
36 outer ledge
37 resilient arm
40 plunger 41 distal end
42 proximal end
42.1 bearing surface
42.2 radial surface
42.3 ramp
43 stem
50 finger flange
51 support portion
52 central portion
53 support surface
54 outer radial surface
55 inner radial surface
60 cap
61 cylindrical portion
61.1 thru hole
62 disc portion
62.1 thru hole
63 gripping surface
63.1 proximal portion
63.2 distal portion
63.2.1 ramp feature
70 hole
71 central recess
71.1 bearing surface
71.2 retaining wall
71.3 protrusion
72 resilient clip
73 lateral recess
500 finger flange
501 support portion
502 central portion
503 support surface
504 outer radial surface
505 inner radial surface
R radial distance inner surface of the cylindrical portion to form an inner gripping surface adapted to frictionally engage the needle shield on the needle, and wherein the outer portion is disposed on an outer surface of the cylindrical portion and a proximal surface of the disc portion.

2. The cap according to claim 1, wherein the gripping member further comprises a distal portion disposed on a distal surface of the disc portion.

3. The cap according to claim 1, wherein the gripping member is made from a first material, and the cylindrical portion and the disc portion are made from a second material, and wherein the first material has a lower durometer than the second material.

4. The cap according to claim 1, wherein at least one of the inner portion or the outer portion of the gripping member includes one or more frictional features disposed on a surface of the inner portion or a surface of the outer portion.

5. The cap according to claim 1, wherein the inner portion of the gripping member has a gripping surface disposed on the inner surface of the cylindrical portion, wherein a thickness of the inner portion of the gripping member decreases from a distal end of the inner portion to a proximal end of the inner portion, and wherein the thickness is measured in a direction along the first outer diameter of the cylindrical portion.

6. The cap according to claim 1, wherein the inner portion of the gripping member includes a ramp feature on a proximal end of the inner portion.

7. The cap according to claim 1, further comprising an indicia located on one or more of the cylindrical portion, the disc portion, or the gripping member.

8. The cap according to claim 7, wherein the indicia includes a word or a symbol.

9. The cap according to claim 1, wherein the disc portion has a circular cross section.

The invention claimed is:

1. A cap for covering a needle shield on a needle of a medicament container, the cap comprising:
 a body comprising:
  a cylindrical portion having a first outer diameter; and
  a disc portion extending outwardly from a distal end of the cylindrical portion, the disc portion having a second outer diameter larger than the first outer diameter of the cylindrical portion; and
 a gripping member having an inner portion and an outer portion, wherein the inner portion is disposed on an 10. The cap according to claim 1, wherein a distal end of the cap is closed.

11. A medicament container comprising:
 a barrel;
 a needle disposed on a distal end of the barrel;
 a needle shield coupled to the needle; and
 a cap coupled to the needle shield, wherein the cap comprises:
  a body comprising:
   a cylindrical portion having a first outer diameter measured in a first direction; and a disc portion extending outwardly from a distal end of the cylindrical portion, the disc portion having a second outer diameter measured in the first direction, wherein the second outer diameter is larger than the first outer diameter; and a gripping member having an inner portion and an outer portion, wherein the inner portion is disposed on an inner surface of the cylindrical portion to form an inner gripping surface adapted to frictionally engage the needle shield on the needle, and wherein the outer portion is disposed on an outer surface of the cylindrical portion and a proximal surface of the disc portion.

12. The medicament container according to claim 11, wherein the gripping member is made from a first material, and the cylindrical portion and the disc portion are made from a second material, wherein the first material has a lower durometer than the second material, and wherein the needle shield comprises a sheath made from a third material.

13. The medicament container according to claim 12, wherein the needle shield comprises a casing made from a fourth material different from the third material and is disposed on the sheath.

14. The medicament container according to claim 13, wherein the third material is made of at least one of rubber or elastomer latex, and the fourth material is made of at least one of polypropylene or acrylonitrile butadiene styrene.

15. The medicament container according to claim 11, wherein the inner portion of the gripping member includes a gripping surface disposed on the inner surface of the cylindrical portion, wherein a thickness of the inner portion of the gripping member decreases from a distal end of the inner portion to a proximal end of the inner portion, and wherein the thickness is measured in a direction along the first outer diameter of the cylindrical portion.

16. The medicament container according to claim 11, wherein at least one of the inner portion or the outer portion of the gripping member includes one or more frictional features disposed on a surface of the inner portion or a surface of the outer portion.

17. A method of using a medical delivery device comprising:

gripping an outer portion of a cap of the medical delivery device, wherein the outer portion of the cap comprises:
a body comprising:
a cylindrical portion, and
a disc portion extending outwardly from a distal end of the cylindrical portion with a diameter larger than a diameter of the cylindrical portion, and
a gripping member having an inner portion disposed on an inner surface of the cylindrical portion to form an inner gripping surface, wherein the cap is coupled with a needle shield covering a needle of the medical delivery device; and pulling the cap from the medical delivery device, wherein pulling the cap causes friction between the inner gripping surface and the needle shield and pulls the needle shield off the needle.

18. The method of claim 17, wherein the inner portion and the outer portion of the cap are made from a first material, and the rest of the cap is made of a second material, and the first material has a lower durometer than the second material.

19. The method of claim 17, wherein the needle shield is made of at least one of rubber or elastomer latex.

20. The method of claim 17, wherein the inner portion of the cap includes a gripping surface disposed on the inner surface of the cylindrical portion, wherein a thickness of the inner portion of the gripping member decreases from a distal end of the inner portion to a proximal end of the inner portion, and wherein the thickness is measured along the diameter of the cylindrical portion.

\* \* \* \* \*

SEQUENCE LISTING

```
<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Exendin-4(1-39), insulin analogue or derivative

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```